Figure 1:
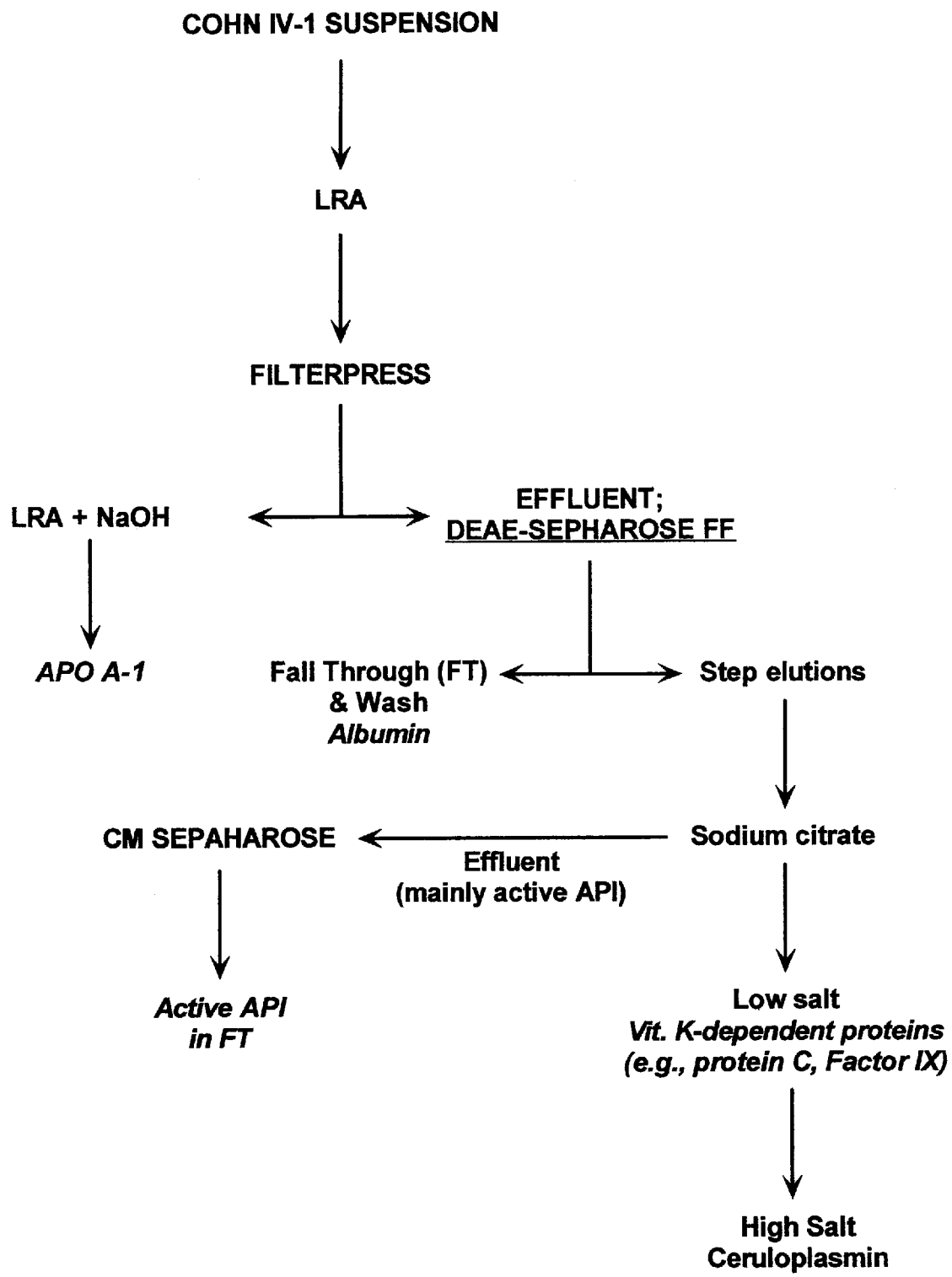

United States Patent [19]
Ralston et al.

[11] Patent Number: 6,093,804
[45] Date of Patent: Jul. 25, 2000

[54] METHOD FOR PURIFICATION OF ALPHA-1 PROTEINASE INHIBITOR

[75] Inventors: Annemarie H. Ralston, Bethesda, Md.; William H. Drohan, Springfield, Va.

[73] Assignee: American National Red Cross, Falls Church, Va.

[21] Appl. No.: 09/159,461

[22] Filed: Sep. 24, 1998

[51] Int. Cl.$^7$ .......................... C07K 14/00; A61K 35/14; A23J 1/00
[52] U.S. Cl. .......................... 530/416; 530/380; 530/392; 530/393; 530/395; 530/412; 530/427; 530/830
[58] Field of Search ................ 530/416, 380, 530/392, 393, 395, 412, 427, 830

[56] References Cited

U.S. PATENT DOCUMENTS

| | | | |
|---|---|---|---|
| 3,293,236 | 12/1966 | Schultze | 530/392 |
| 4,379,087 | 4/1983 | Coan et al. | 530/380 |
| 4,439,358 | 3/1984 | Coan et al. | 530/380 |
| 4,656,254 | 4/1987 | Shearer et al. | 530/393 |
| 4,697,003 | 9/1987 | Coan | 530/380 |
| 4,749,783 | 6/1988 | Jordan et al. | 530/393 |
| 5,610,285 | 3/1997 | Lebing et al. | 530/416 |

FOREIGN PATENT DOCUMENTS

| | | |
|---|---|---|
| 8-99999 | 4/1996 | Japan . |
| WO97 48422 | 12/1997 | WIPO . |
| WO97 48482 | 12/1997 | WIPO . |
| WO97/48422 | 12/1997 | WIPO . |
| WO97/48482 | 12/1997 | WIPO . |

OTHER PUBLICATIONS

David A. Johnson et al., "Human Alpha–1–Proteinase Inhibitor Mechanism of Action: Evidence for Activation by Limited Proteolysis", Biochem. Biophys. Res. Comm vol. 72, No. 1, pp. 33–39, (1976).

Eric G. Del Mar et al., "Effect of Oxidation of Methionine in a Peptide Substrate for Human Elastes: A Model for Inactivation $\alpha_1$–Protease Inhibitot", Biochem. Biophys. Res. Comm, vol. 88, No. 2, pp. 346–350, (1979).

G. Wright et al., "High Level Expression of Active Human Alpha–1–Antitrypsin in the Milk of Transgenic Sheep", Biotechnology, vol. 9, pp. 830–834 (1991).

A.L. Archibald et al., "High–level Expression of Biologically Active Human Alpha–1–Antitrypsin in the Milk of Transgenic Mice", Proc. Nat'l. Acad. Sci. USA., vol. 87, pp. 5178–5182 (1990).

Kress et al., "Large Scale Purification of Alpha–1 Trypsin Inhibitor From Human Plasma" Preparative Biochemistry, vol. 3, No. 6, pp. 541–552 (1973).

Dubin et al., Prep. Biochemm. 20: 63–70 (1990).

Hao et al., Proceedings of the International Workshop on Technology for Protein Separation and Improvement of Blood Plasma Fractionation, Sep. 7–9, 1977, Reston, Virginia.

Hein et al., Production of $Alpha_1$–Proteinase Inhibitor (Human) Eur. Respir. J. 9: 16s–20s (1990).

Burnouf et al., "Biochemical and Biological Properties of an $\alpha_1$–Antirypsin Concentrate", Vox. Sang. 52: 291–297 (1987).

Podiarene et al., Vopr. Med. Khim. 35:96–99 (1989) (in Polish with English Abstract).

Glaser et al., "Isolation and Characterization of Alpha–1–Antitrypsin From the Cohn Fraction IV–1 of Human Plasma" Preparative Biochemistry, vol. 5, No. 4, pp. 333–348 (1975).

*Primary Examiner*—Christopher S. F. Low
*Assistant Examiner*—Abdel A. Mohamed
*Attorney, Agent, or Firm*—Burns, Doane, Swecker & Mathis, L.L.P.

[57] ABSTRACT

The methods of the present invention provide a simple means for separating active and inactive Alpha Proteinase Inhibitor (API). The methods further provide means for purifying API at high yield (>70%), and at levels of purity (>90%) and activity (>90%) not heretofore available. Moreover, the methods of the present invention are simple (i.e., two chromatographic steps) and efficient; and are thus especially suitable to large scale purification processes. These methods will contribute substantially to alleviating the unmet demand for API for therapeutic purposes.

33 Claims, 1 Drawing Sheet

METHOD FOR PURIFICATION OF ALPHA-1 PROTEINASE INHIBITOR

BACKGROUND OF THE INVENTION

I. Field of the Invention

The present invention provides a process for protein purification, specifically a process for purifying alpha-1 proteinase inhibitor (or alpha-1 antitrypsin or "API") from blood plasma or blood plasma fractions. The present invention further provides formulations of 100% active API.

II. Technology Background

Alpha-1 proteinase inhibitor is a glycoprotein having molecular weight of 53,000. API has a role in controlling tissue destruction by endogenous serine proteinases, and is the most pronounced serine protease inhibitor in blood plasma. In particular, API inhibits various elastases including neutrophil elastase. See Biochem. Biophys. Res. Comm., Vol. 72, No. 1, pages 33–39, (1976); ibid., Vol. 88, No. 2, pages 346–350, (1979).

Elastase is a proteinase which breaks down tissues, and can be particularly problematic when its activity is unregulated in lung tissue. This protease functions by breaking down foreign proteins. However, when API is not present in sufficient quantities to regulate elastase activity, the elastase breaks down lung tissue. In time, this imbalance results in chronic lung tissue damage and emphysema. In fact, a genetic deficiency of API has been shown to be associated with premature development of pulmonary emphysema. API replenishment has been successfully used for treatment of this form of emphysema.

A deficiency of API may also contribute to the aggravation of other diseases such as cystic fibrosis and arthritis, where leukocytes move in to the lungs or joints to fight infection. With a deficiency in API, uninhibited lymphocyte elastase may result in destruction of the surrounding tissue. Thus, API could conceivably be used to treat diseases where an imbalance between inhibitor and protease(s), especially neutrophil elastase, is causing progression of a disease state. Antiviral activity has also been attributed to API.

Purified API has been approved by the FDA for chronic replacement therapy in individuals with congenital deficiency for the treatment of panacinar emphysema. The existing API market is under-supplied; while research suggests additional therapeutic uses for API. For example, studies suggest API might be useful against tissue destruction by uncontrolled neutrophil elastase activity. Such research is hindered by lack of supply. More efficient means of isolation, or alternative sources, of API are required.

Several groups have reported production of recombinant API. See, e.g., G. Wright et al., "High Level Expression of Active Human Alpha-1-Antitrypsin in the Milk of Transgenic Sheep", Biotechnology, Vol. 9, pp. 830–834 (1991); and A. L. Archibald et al., "High-level Expression of Biologically Active Human Alpha-1-Antitrypsin in the Milk of Transgenic Mice", Proc. Nat'l. Acad. Sci. USA., Vol.87, pp. 5178–5182 (1990). However, human plasma is the only approved source of therapeutic API. Anticipated API demand is shown in Table 1.

TABLE 1

Anticipated demand for API.

| Treatment (& type of administration) | # Patients | Yearly Dose (g) | Product Needs (kg) |
|---|---|---|---|
| Congenital Deficiency (Intravenous) | 1,700 | 218 | 370 |
| Cystic Fibrosis - U.S. (Aerosol) | 30,000 | 75 | 2,250 |
| COPD, ARDS, Emphysema (not PiZZ) (Aerosol)[1] | >5,000,000 | variable | large |
| Psoriasis (Topical) | 235,000 | 12 | 2,830 |

[1]COPD = Chronic Obstructive Pulmonary Disease
ARDS = Adult Respiratory Disease Syndrome
PiZZ = hereditary form of API deficiency resulting from a point mutation in the gene for API Combined human plasma sources produce approximately 7,000,000 L of human plasma per year. Every one million liters of plasma produces about 20,000 kg of Cohn Fraction IV-1 paste. And every kg of Cohn Fraction IV-1 paste contains between 15 and 20 g of API. Thus, even if API could be isolated at 100% efficiency and activity from all available human sources, there would still not be enough to meet demand.

As it is, existing isolation and purification processes are inadequate. Trace impurities resulting from inefficient purification processes can stimulate an immune response in patients. Furthermore, purification processes that fail to separate active and inactive API can lead to a product with unpredictable efficacy and a specific activity which varies between separate lots. PROLASTIN™ (Miles, Inc.) is the only plasma-derived, FDA-approved product presently on the market. However, this product is not completely pure, and typically contains about 12% albumin and 2.5% IgA, and is only 60% active.

A number of methods have been employed to isolate API from the blood plasma. A majority of these methods are directed to laboratory scale isolation while others pertain to production on a commercial level. Several methods of isolation are summarized in U.S. Pat. Nos. 4,379,087 and 5,610,285, which are incorporated by reference. Many early methods employed ammonium sulfate precipitation from human plasma and dialysis, followed by a subsequent chromatographic step on DEAE-cellulose. However, dialysis is not easily applicable to large scale purification, and is a lengthy, time consuming process likely to compromise activity of the isolated protein.

A large scale purification of API from human plasma was disclosed by Kress et al., Preparative Biochemistry, Vol. 3, No. 6, pages 541–552 (1973). The precipitate from the 80% ammonium sulfate treatment of human plasma was dialyzed and chromatographed on DEAE-cellulose. The concentrate obtained was again dialyzed and gel filtered on SEPHADEX® G-100. The API-containing fractions were chromatographed twice on DE-52 cellulose to give API.

Glaser et al., Preparative Biochemistry, Vol. 5, No. 4, pages 333–348 (1975) isolated API from Cohn Fraction IV-1. In this method, dissolved IV-1 was chromatographed on DEAE-cellulose, QAE-SEPHADEX®, concanavalin A-SEPHAROSE®, and G-150 SEPHADEX® to give API. However, Glaser et al. achieved only a 30% overall yield.

Podiarene et al., Vopr. Med. Khim. 35:96–99 (1989) reported a single step procedure for isolation of API from human plasma using affinity chromatography with monoclonal antibodies. API activity was increased 61.1 fold with a yield of only 20%.

Burnouf et al., Vox. Sang. 52: 291–297 (1987) starting with Cohn Fractions II+III used DEAE chromatography and size exclusion chromatography to produce an API which was 80–90% pure (by SDS-PAGE) with a 36-fold increase in purity. Recovery was 65–70% from the supernatant A.

Hein et al., Eur. Respir. J. 9: 16s–20s (1990) presented a process that employs Cohn Fraction IV-1 as the starting material and utilized fractional precipitation with polyethylene glycol followed by anion exchange chromatography on DEAE SEPHAROSE®. The final product has a purity of about 60% with 45% yield.

Dubin et al., Prep. Biochem. 20: 63–70 (1990) used a two step chromatographic purification whereby alpha-PI, $C_1$-inhibitor, alpha-1 antichymotrypsin, and inter alpha-1 trypsin inhibitor were first eluted from Blue SEPHAROSE® and then API was purified by gel filtration. Purity and yield data were not given.

Jordan et al., U.S. Pat. No. 4,749,783 (1988) described a method where biologically inactive proteins in a preparation were removed by affinity chromatography after a viral inactivation step. The basis of the separation between the native and denatured forms of the protein was the biological activity of the native protein towards the affinity resin and not physical differences between the native and denatured proteins.

An integrated plasma fractionation system based on polyethylene glycol (PEG) was disclosed by Hao et al., Proceedings of the International Workshop on Technology for Protein Separation and Improvement of Blood Plasma Fractionation, Sept. 7–9, 1977, Reston, Va. In the published method Cohn cryoprecipitate was mixed with increasing concentrations of PEG in order to obtain four different PEG fractions. The four fractions obtained were 0–4% PEG precipitate, 4–10% PEG precipitate, 10–20% PEG precipitate and 20% PEG supernatant. The 20% PEG supernatant fraction was dominated by albumin but also contained most of the API. However, this fraction also contained numerous other proteins, including all of the alpha-1-acid glycoprotein, antithrombin III, ceruloplasmin, haptoglobin, transferrin, Cl esterase inhibitor, prealbumin, retinol binding protein, transcortin, and angiotensinogen.

Several other groups have combined PEG precipitation with other purification methods in an attempt to isolate API. For instance, U.S. Pat. No. 4,379,087, U.S. Pat. No. 4,439,358, U.S. Pat. No. 4,697,003 and U.S. Pat. No. 4,656,254, all employ a PEG precipitation step in processes of isolating API. PEG precipitation is disadvantageous in that PEG will also precipitate hepatitus B virus. Although viruses are typically inactivated in a heat pasteurization step following purification of API, precaution must be taken, and patients must therefore be immunized before receiving treatments.

Along with PEG precipitation, U.S. Pat. No. 4,379,087 by Coan et al. also reports a concentration step involving phosphate buffer and DEAE SEPHAROSE™. The combined process is quite lengthy, i.e., five days. Furthermore, the final product is only 60% active and only 80% pure.

Japanese Patent No. 8-99999 describes using PEG precipitation in combination with an SP-cation exchanger. The methods described therein do not separate fully active API from inactive API. The specific activity of fully active API should be 1.88 (using an Extinction coefficient 5.3), but the product achieved by this process only shows a relative activity of 1.0. Moreover, the best yield, achieved by combining PEG precipitation and SP-cation exchange steps, was only 50%, and does not appear to be easily scaled up to a commercial production level.

U.S. Pat. No. 3,293,236 describes a process for purifying API using citrate buffered cation exchange chromatography, and combines this step with fractionation of human plasma with ammonium sulfate. The importance of the DEAE purification step of the present invention becomes apparent when one examines the yields reported in U.S. Pat. No. 3,293,236. The yields were not measured by specific activity of API, and the reported quantities of protein equate to much more API than is initially present in human plasma. Thus, the product achieved by the method disclosed in U.S. Pat. No. 3,293,236 must have a high quantity of contaminating protein.

U.S. Pat. No. 5,610,285 discloses a purification process which combines successive anion and cation exchange chromatography steps. The initial anion exchange chromatography step binds API to the column; however, it also binds numerous contaminating proteins, particularly lipoproteins. Lipoproteins are plentiful in many of the materials from which API is isolated (e.g. Cohn IV paste), and so tend to occlude the column. Such occlusion requires columns of considerable size, additional dialysis/filtration steps, and at least two cation chromatography steps. Those requirements reduce efficiency and practicality of the method for large-scale processes.

Further, in the '285 process all API, both inactive and active protein, bind to the anion exchange column. And when the API is eluted from that column in accordance with that method, i.e., high salt phosphate buffer, both active and inactive protein come off the column. Thus, there is no separation of the active from the inactive protein.

III. SUMMARY OF THE INVENTION

Demand for API exceeds available supply. To maximize use of our limited available resources of this precious commodity, we need an API purification process that produces pure, active API in good yield, and one that is cost-efficient and suitable for large scale application. The present invention provides such a process. It is a particular advantage of the present invention that the purification process includes an elegant and unexpected means for separating active from inactive API.

The American Red Cross (ARC) processes nearly one million liters of human plasma annually by the Cohn ethanol fractionation method for the production of a number of products. Among other by-products of Cohn fractionation, the ARC collects approximately 17,000 kg of Cohn Fraction IV-1, containing between 15–20 g of API per kg of paste. ARC thus has the ability to make a significant contribution to the quantity of API available for therapeutic use.

We have found that the separation of active from inactive API can be achieved in a single separation process on an anion exchange column. Further purification can be achieved by passing the eluate of the anion exchange step through a cation exchange resin. Thus, the present invention provides a means for achieving high yield isolation and purification of active API from various sources. Generally, the method involves the removal of lipoproteins from an initial protein suspension by use of a lipid removal agent (also referred to herein as "LPA"), followed by successive separations with anion and cation exchange resins with specific eluants.

The processes of the present invention provide an improvement over other processes. The present process provides API with a product purity of >90%; and yield at manufacturing scale of >70%. Moreover, of all the API collected by the present method, greater than 90% of it is in its active form. In fact, the method of the present invention can produce API isolates having greater than about 95% active API; and can be as much as 100% active.

The method of the present invention compares favorably with other methods. For example, the process of the present invention provides a 40-fold purification, and results in an API product having a specific activity of >1.85 (See Table 9); whereas, for example, the process of Japanese Patent No. 8-99999 reportedly provides only a 15-fold purification. Further, the present method can produce 100% active API of over 90% purity; whereas, for example, the method of the '285 patent produces a mixture of active and inactive API that is only 60–70% pure after the first cation exchange step.

While several other groups have described either anion or cation exchange in combination with other types of purification steps, no other process describes such a simple and efficient method for isolating API having such a high level of purity and activity. The simplicity and efficiency of the present method makes it especially suitable for application on a large scale, and thus will contribute substantially to meeting the needs for API for therapeutic purposes.

The present invention includes a means for separating active from inactive API on an anion exchange resin. The API-containing protein mixture is first suspended in a non-citrate buffer, such as a phosphate buffer, treated with a lipid removal agent and filtered or otherwise clarified. The clarified phosphate buffer-protein mixture is contacted with an anion exchange resin, and the resin is washed to remove contaminants. Active API is then removed (eluted) from the anion exchange resin with a citrate buffer. The API eluted is greater than 90% active. Removal of lipoproteins with LRA in this process is particularly advantageous as it substantially reduces the quantity of contaminants, and so reduces the requisite quantity of solvents and anion exchange resin, as well as the size of the columns or beds, thereby imparting substantial efficiencies.

Preferably, an additional separation step is introduced involving a cation exchange step. The cation exchange separation step is introduced to eliminate remaining contaminants after the isolation of the active API. The cation exchange step is carried forward in a citrate buffer. The active API appears in the flowthrough, while the various remaining contaminants, such as albumin, APO-A1, alpha-2 macroglobulin and the like, are bound to the resin. The effluent of the citrate wash of the cation exchange resin thus produces nearly pure, active API in high yield (i.e., >70%).

An API purification process according to the present invention thus involves (i) suspension of an API-containing protein mixture in a non-citrate buffer; (ii) removal of lipoproteins from that mixture with a lipoprotein removal agent,(iii) contacting the resulting mixture with an anion exchange resin, wherein active API is bound to the resin; (iv) eluting active API from the anion exchange resin; and (v) passing active API through a cation exchange resin.

The objects and further particulars of the present invention will be evident by the following description. All publications and patent applications referenced herein are incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, the term "elution" refers to removal of a species bound to a substrate such as an ion exchange resin; the term "eluate" refers to a solvent mixture containing the species removed from such a substrate; and the term "effluent" refers more generally to any material or mixture emerging from a column, container, or reservoir.

IV. BRIEF DESCRIPTION OF THE DRAWINGS

FIG. 1 is a flow chart illustrating schematically the API purification process of the present invention, and means for isolating other therapeutic biological materials that are by-products of the API purification process.

V. DETAILED DESCRIPTION OF THE INVENTION

A particular advantage of the present invention is a simple and elegant separation of active from inactive API. We have discovered a means for the complete or near complete separation of the two forms of the protein in a single chromatographic step. We have surprisingly discovered that active API is preferentially bound to an anion exchange resin in non-citrate buffer, such as Tris or phosphate buffer, within a particular pH range; and that it is preferentially eluted from the anion exchanger by citrate buffer in a particular pH range. This simple separation process routinely produces API fractions having greater than 90% active API. Once the inactive API is separated from the active API, additional separation steps can be effected to eliminate remaining contaminants such as albumin, APO-A1, alpha-2 macroglobulin and the like.

According to the present invention, a method for separating active from inactive API includes the steps of (i) suspending an unpurified mixture of proteins containing both active and inactive API in a phosphate buffer at a pH of at least about 8.0; (ii) adjusting the pH of the suspension to about 5.8 to about 6.4 and promptly removing lipoproteins from said suspension with a lipid removal agent (e.g., CHROMOSORB E or MICRO CEL E, World Minerals, Inc., 137 West Central Avenue, Lompoc, Calif.); (iii) removing the LRA and lipoprotein and re-adjusting the pH of the suspension to a pH of about 5.8 to about 6.4; (iv) loading the pH adjusted suspension onto an anion exchanger and washing with a phosphate based buffer; and (iv) eluting bound active API from the anion exchanger with a citrate buffer at a pH of about 5.8 to about 6.4.

This simple, single chromatographic separation provides API fractions of at least about 90% active API; often providing fractions of greater than about 95% active API; and can achieve fractions of 100% active API. No other method has afforded such complete separation of active and inactive API in such a cost-effective and efficient manner as the method of the present invention.

The present invention further affords facile methods for purifying active API to levels greater than 90% purity. Such methods comprise: (i) suspending an unpurified mixture of proteins containing API in a phosphate buffer at a pH of about 8.0; (ii) adjusting the pH of the phosphate buffer suspension to a pH of about 5.8 to about 6.4 and removing lipoproteins from said protein suspension with lipid removal agent; (iii) re-adjusting the pH of the phosphate buffer suspension to a pH of about 5.8 to about 6.4, loading the resulting protein suspension on an anion exchange resin, and washing said resin with a phosphate based buffer; (iv) eluting active API from said resin with a citrate based buffer; (v) adjusting the eluate of step (iv) to a pH of less than about 5.6 and a conductivity of less than about 1.7 mmho; (vi)

contacting said eluate with a cation exchange resin, and washing active API through said resin with a similarly pH- and conductivity-adjusted citrate buffer.

The methods of the present invention optionally further include a step wherein the purified API solution is subjected to viral reduction following purification. Viral reduction can be accomplished by sever al processes, including nanofiltration; solvent/detergents; iodine inactivation, e.g., treatment with an iodinated ion exchange matrix material such as iodinated SEPHADEX® (also referred to herein as "IODINE SX" and as disclosed in PCT applications WO97 48422 and WO97 48482); treatment with Pathogen Inactivating Compositions (also referred to as "PICs", and as disclosed in "Pathogen Inactivating Compositions for Disinfecting Biological Fluids" Ser. No. 09/159,460, filed Sep. 24, 1998, the disclosure of which is incorporated hereby by reference)s; heat inactivation; gamma irradiation; or any other suitable virucidal process. A combination of (i) nanofiltration and (ii) IODINE SX or PIC treatment is preferred.

The unpurified mixture of proteins from which the API is collected is preferably Cohn Fraction IV-1 paste, but can include other Cohn Fractions, separately or in combination, human blood plasma, plasma fractions, or any protein preparation containing API. For instance, the present method is applicable to purification of recombinant human API from the milk of transgenic animals. (When milk is used as starting material, an ammonium sulfate or sodium chloride precipitation step is first employed to separate API from caseins, and the precipitate is taken through the present purification process.)

A particular advantage of the present invention is the ready elimination of contaminants or by-products that otherwise compromise the efficiency of API purification processes. Cohn Fraction IV-1 preparations in particular contain a significant amount of APO A-1, which has the effect of inhibiting column flow and capacity during purification. Treatment of the protein mixture suspension with LRA removes APO A-1 and >40% of impurities from Cohn Fraction IV-1 plasma preparations. Hence, removal of APO A-1 and contaminating proteins—without loss of API— enables a significant reduction in equipment, e.g., column size. This step also enables isolation of APO A-1, which is useful in the treatment of septic shock. APO A-1 may be recovered with 0.5 N NaOH for downstream processing.

The methods of the present invention can utilize many of the various non-citrate based buffers, e.g., Tris or a phosphate buffer. Preferably, sodium phosphate buffer is used wherein said buffer is kept at a pH of between about 6 and about 9 throughout the process. Discrete manipulations within that range are preferable throughout the process. For example, the suspension of the protein-containing mixture in buffer solution should be done at a pH of about 8.0, and at a ratio of between about 10 to about 30 L per about 1 kg of Cohn Fraction IV-1 paste. A preferred method uses a ratio of 15 L per 1.0 kg of paste, and a buffer concentration of 15 to 25 mM. However, it should be apparent to those familiar with the art that the pH and molarity of the buffer, and the ratio of buffer to Cohn Fraction IV-1 may be varied by routine optimization depending on the qualities of the starting material.

The pH required for suspension of the starting material and the optimal pH for chromatography may be different, in which case the pH of the suspension is adjusted before column loading. For loading on the anion exchange resins as described herein, the suspension is preferably adjusted to a pH of between about 5.4 and about 7, but more preferably to a pH of between about 5.8 and about 6.4, and most preferably to a pH of 6.0±0.1.

When used at the appropriate pH, the anion exchange resin reversibly binds active API from the protein mixture (e.g., Cohn Fraction IV-1). Also captured along with API are vitamin K proteins, which can be purified separately by adjusting the characteristics of the elution buffer. Active API preferentially binds to the anion exchange column when applied in phosphate buffer at a pH of about 6. (When the pH is raised to about 8, for instance, significant quantities of contaminating protein also bind to the column, and reduce the purity of the product of the process.)

Any anion exchange resin will likely be useful in the processes of the present invention. Common anion exchange resins useful in the methods of this invention include those formed of agarose, cellulose, and acrylamide, and variations thereof such as cross-linked agarose and cross-linked cellulose. Particularly preferred resins are those wherein the anion exchange functionality is provided by a tertiary or quaternary amine derivatization of the resin. Examples include DEAE SEPHAROSE® FAST FLOW (hereinafter, DSFF), DEAE SEPHAROSE® CL-6B, and Q SEPHAROSE® FAST FLOW. DSFF is especially preferred.

The optimal pH of the equilibration and elution buffers will vary depending on the resin, size of column or bed, and the buffer used.

Adjusting the flow through the resin such that the residence time is preferably between 8 and 10 minutes is generally sufficient to enhance displacement of albumin by API. However, it should be clear that a wide range of flow rates are possible depending on the quantity and quality of product desired.

Elution of bound API may be accomplished with any citrate buffer, but is preferably performed with sodium citrate. For proper elution, the sodium citrate should be at a pH of between about 5.5 and about 8.5 depending on the pH of the phosphate buffer used for column equilibration. Most preferably, the sodium citrate buffer solution is about pH 6.0.

Depending on the pH used for elution, the pH of the eluate might need to be adjusted before being loaded onto the cation exchanger. Generally, for cation exchange chromatography, the pH of the eluate applied to the cation exchanger should not be above 5.6, otherwise albumin contamination will result. Thus, running the column with a pH that is too high will compromise purity. More preferably, the pH is between about 5 and 5.5 depending on the type of cation exchange column used.

Optimally, the conductivity of the active API-containing eluate of the anion exchange column is likewise adjusted prior to separation on the cation exchange resin. Conductivity of the eluate should be less than about 1.7 mmho; preferably about 0.9 to about 1.6 mmho, and most preferably about 1.3 to about 1.45 mmho.

In a citrate based buffer, cation exchange resins capture contaminants while API is recoverable in the effluent (fall-through). Good yield and purity are achieved with any suitable weak cation exchange resin, including CM SEPHAROSE® FAST FLOW, CM SEPHAROSE® CL-6B, SP SEPHAROSE® FAST FLOW, FRACTOGEL EMD $SO_3^-$-650 (M) and WHATMAN-CELLULOSE® columns, for example. Again, the optimal pH and molarity of the equilibration and running buffers will vary depending on the particular column used, but are easily optimized within the parameters supplied herein. CM SEPHAROSE® FAST FLOW equilibrated with about 3 to 10 mM sodium citrate, preferably about 5 mM sodium citrate, at a pH of 5.35±0.15 is preferred. Recommended residence time of CM-SEPHAROSE® is at least 15–30 minutes, but may be modified according to time constraints and the level of purity desired without drastically affecting the resulting product.

Although post-washes may be performed after either chromatography step, because API is in the fall-through following cation exchange chromatography, post-washes following this step can result in quantitative recovery of API. It is generally preferred to perform a post-wash with one column volume of sodium citrate buffer at about the same pH as the adjusted effluent and the equilibration buffer. The fall-through and the post-wash are combined before viral inactivation and/or formulation.

The methods of the present invention give highly purified API with only two chromatographic separation steps with near quantitative yields; and yields in large-scale processes exceed 70%. The resulting API preparation is at least about 90% pure and about 100% active. Thus, the method of the present invention presents an improvement over methods as well as a more practical and efficient way of isolating API. The API suspension produced by the method described herein is also encompassed in the present invention.

As described above, the method of the present invention can be applied to various API-containing proteinaceous starting materials (e.g., Cohn Fraction IV-1 paste). For instance, the same chromatographic steps can be used to purify API from the milk of transgenic animals after the milk proteins are removed in an initial precipitation step using ammonium sulfate or sodium chloride. Precipitation conditions for milk caseins vary depending on the species. The present inventors have evaluated these precipitation conditions by spiking plasma-derived API into the milk of cow, pig and goat. Optimal conditions are compared in Table 2.

TABLE 2

Precipitation conditions for purifying recombinant API from the milk of transgenic animals[1]

| Precipitating Agents | Goat Milk | Pig Milk | Cow Milk |
| --- | --- | --- | --- |
| Ammonium sulfate (final conc.)[2] | 2.0 ± 0.1 M | 2.05 ± 0.1 M | 1.53 ± 0.05 M[3] |
| Sodium chloride (final conc.) | NA | NA | 5.0 M[3] |

[1]Process evaluated with human API spiked into the milk of goats, pigs and cows; milk fats removed by centrifugation prior to precipitation; precipitation performed at 4–10° C.; API remains in the supernatant.
[2]By addition of solid ammonium sulfate
[3]By addition of saturated ammonium sulfate or sodium chloride solution.

In the process of the present invention, LPA is used to remove lipoproteins prior to DEAE chromatography. This step removes APO A-1 and >40% of impurities from Cohn Fraction IV plasma preparations. Cohn Fraction IV preparations in particular contain a significant amount of APO A-1, which limits the column performance drastically during purification. Hence, removal of APO A-1 enables a significant reduction in column size, resulting in a more economical and simplified process on a large scale.

For instance, pretreatment with LRA reduces DSFF column volume from about 100–120 L to about 55–70 L, and reduces CM-SEPHAROSE® column volume from about 240–280 L to 110–140 L. The differences in total column volumes, washes and effluents with and without LRA for the process of the present invention are shown in Table 3.

TABLE 3

Differences in column volumes with and without LRA treatment

| Column | With LRA[+] | Without LRA |
| --- | --- | --- |
| DSFF Column Volume (L) | 55–70 | 100–120 |
| Dissolution Volume (L) | 1050 | 1050 |
| Wash (L) | 600–900 | 1000–2000 |
| DSFF Effluent (L) | 140–180 | 250–300 |
| CM-SEPHAROSE ® Column (L) | 110–140 | 240–280 |
| CM-Load (L) | 350–450 | 600–900 |
| Fallthrough - (L) | 460–650 | 900–1300 |

[+]LRA or CHROMOSORB E (MICRO CEL E)

LRA treatment adds the advantage of allowing separate purification of APO A-1, which has separate utility in the treatment of septic shock. APO A-1 will be captured nearly quantitatively by LRA or CHROMOSORB E and can be recovered with 0.5 N NaOH for downstream processing.

Some other advantages of the present process are that solvent/detergent treatment of the Cohn Fraction IV-1 suspension can be executed without impact on the process, and the process is also applicable with minor changes (reduction of resin volumes) to other Cohn Fraction sources of similar composition (e.g., Cohn Fractions I+III). Furthermore, the process may be completed in 20–22 hours for a 70 kg manufacturing lot, and active API is selectively purified over non-active protein.

The preferred conditions of the present methods are as follows:

A. Solubilization of Cohn Fraction IV-1 Paste

Cohn Fraction IV-1 paste containing at least 10 g/kg to 25 g/kg of $a_1$-Proteinase Inhibitor (API) is broken carefully into small pieces without letting the paste thaw. The pieces are rapidly suspended with stirring in 15 mM sodium phosphate buffer, pH 8.1±0.1 at 15–20° C. For every kilogram of input paste, 15 liters of buffer are required. The slurry is stirred for at least 5 hours at +25–30° C., preferably overnight. After dissolution the pH is carefully adjusted to 6.0±0.1 with 0.3–0.5 M HCl.

B. Treatment of Cohn Suspension with LRA

LRA (CHROMOSORB E; World Mineral) is added to the suspension at 4% (w/w; 40 g/kg). The slurry is stirred for 1 hour at +15–20° C. LRA at this concentration and under these pH conditions captures, without any loss of API, 50% of the contaminating proteins and removes APO-A1 and lipoproteins. Removal of the LRA and contaminating proteins is performed by filtration. This removal of lipoprotein prevents the subsequent loss of binding capacity of the ion-exchange resins otherwise caused by excess contaminating proteins. LRA treatment therefore maintains optimal resin performance for API purification.

LRA may be removed by filter press filtration or centrifugation. For filter press filtration, 0.3–0.5% (w/w; 3–5 g/kg) of Filter Aid 501 FF is added before the precipitate is collected. The filter press is post-washed with 15 mM sodium phosphate buffer, pH 6.0, to obtain a filtrate volume close to the original Cohn suspension volume. For every one kg of LRA added, five kg of filter press cake are to be expected. The combined filtrate/post-wash is carefully pH adjusted with 0.3–0.5 M HCl to pH of about 5.8 to about 6.4, and preferably a pH of 6.0±0.1. The pH adjusted filtrate is loaded onto a DEAE SEPHAROSE® FAST FLOW (DSFF) column through a depth filter of 20μ or less.

C. DEAE SEPHAROSE® FAST FLOW Column (DSFF)

A DSFF column is prepared using 0.8 to 1.0 liters of resin per kilogram of Cohn Fraction IV-1 paste. The DSFF is equilibrated with two column volumes (CV) of 150 mM sodium phosphate, pH 6.0, followed by 15 mM sodium phosphate, pH 6.0, until equilibration is achieved (pH and conductivity), frequently within 3–4 CV with fresh resin. The clarified (e.g., LRA treated and filtered) paste solution is loaded at linear velocity (LV) of 40–60 cm/H. API binds under these conditions strongly to DSFF while displacing other Cohn IV-I contaminants with weaker binding affinity to DSFF under the chosen conditions. API preferably displaces albumin and most of the other proteins, such as alpha-2 macroglobulin, transferrin, and haptoglobulin. DEAE-SEPHAROSE® resins become saturated with API and ceruloplasmin under these loading conditions. Residence times of less than 6 minutes should be avoided to allow API sufficient time to displace albumin.

The DSFF column is washed with eight to ten column volumes of 15 mM sodium phosphate, pH 6.0. However, bench scale studies indicate that washing of the DSFF column with 2 CV of 15 mM sodium phosphate, followed by 6–8 CV of 20 mM sodium phosphate, may remove more contaminating albumin. Washing with 15 mM sodium phosphate at a lower pH of 5.7 could lead as well to a DSFF effluent with less albumin contaminant. The load velocity of the wash is generally between 50–70 cm/H.

The API is eluted with 20 mM sodium citrate, pH 6.0 at a velocity of 25–35 cm/H. Most of the API activity is eluted within 2½ CV.

Sequential step elutions with low and high salt (0.18–0.4M) of the proteins that remained bound to the anion exchange resin after the sodium citrate elution allow the separate recovery of vitamin K-dependent proteins (e.g. protein C, factor IX) from ceruloplasmin. Complete regeneration is accomplished with 4.0 M NaCl and 1.0 M NaOH with 4.0 M NaCl and 1.0 M NaOH and 1.0 M acetic acid. This regenerates the DSFF column, which is then stored in 10 mM acetic acid.

Instead of DSFF, Q-SEPHAROSE® FAST FLOW can be used for the capture step with equal capture capacity for API. However, the elution volume of the Q-SEPHAROSE® is slightly larger.

D. Adjustment of the DSFF Effluent

For loading on the CM SEPHAROSE® column, the DSFF effluent should be adjusted to a conductivity of less than about 1.7 mmho and a pH of less than about 5.6; preferably the conductivity is adjusted to about 0.9 to about 1.6 mmho and pH of about 5.0 to about 5.5; and most preferably a conductivity of about 1.30 to about 1.45 mmho and pH of about 5.30 to about 5.35. This can be done in two different ways:

(1) In the first method, the DSFF effluent is diluted with distilled water to the appropriate conductivity and the pH is carefully adjusted with 0.3–0.5 M HCl while stirring. This is the preferred method, since there is less of a chance of inactivating API in the diluted suspension at the lower API concentration. The adjustment is also achieved very rapidly and avoids diafiltration, a method which is not without its challenges.

(2) In the second method, the conductivity of the DSFF effluent is adjusted by diafiltration without substantial volume change of the DSFF effluent. The pH of the DSFF effluent is then adjusted very slowly with 0.1–0.3 M HCl. The second method has a greater potential to inactivate the API during acidification due to a higher local API concentrations than is in the diluted DSFF effluent. In addition, CM chromatography works better with the less concentrated DSFF effluents.

The first method is preferred, since it is less labor intensive, is cheaper, uses less buffer and is better for maintaining protein integrity.

E. CM SEPHAROSE® Column (CMS)

A CM SEPHAROSE® column is prepared using 1.7 to 2.0 liters of CM SEPHAROSE® per kilogram of input Cohn Fraction IV-1 paste. CM SEPHAROSE® FAST FLOW and CM SEPHAROSE® CL-6B are useful. The CMS is equilibrated in 5 mM sodium citrate at pH 5.35–5.40. We prefer to use approximately 20 CV to ensure proper equilibration, but this quantity may be varied depending on the type of column.

The clarified, pH- and conductivity-adjusted DSFF effluent is loaded at a linear velocity which provides a residence time of a minimum of 15 minutes normally achieved at a linear velocity of 35–50 cm/hr. API falls through the column while contaminants such as albumin, APO A-1, alpha-2 macroglobulin and other contaminants are bound to the resin. A post-wash of 1–1½ CV of 3–5 mM sodium citrate, pH 5.35 is passed through the column and pooled with the fall-through. The post-wash should only be large enough to flush out the remaining load from the CMS. Too large volume of post-wash will otherwise add back contaminants to the fall-through. It is recommended that this step be monitored by absorbance at A280 nm. As API falls through, there is a plateau in the absorbance at A280 nm which is maintained relative to the purity of the fall-through. If the A280 suddenly rises, the capacity of the cation exchange resin has been exceeded and contaminants are beginning to fall through the column along with the API.

The pH of the API pool should be immediately adjusted to pH 6.5–7.0 with 0.5 N NaOH while stirring.

The proteins bound to the cation exchange resin may be removed with 2.0 M NaCl and 1.0 M NaOH and 1.0 M acetic acid. The column is regenerated with 2.0 M NaCl, 1.0 N NaOH and stored in 10 mM NaOH.

F. API Intermediate Product—Viral Reduction

The CMS fall-through will be concentrated to 10–20 mg/ml of API, possibly after viral reduction by filtration. Asahi filters 35 nm, 70 nm, and 15 nm and Pall UDV 50 have been successfully used after prefiltration (A/G Technology). Millipore's VIRESOLVE® Ultrafilters might also be applicable.

The process also provides several other options to implement viral reduction steps. We have evaluated pasteurization, solvent/detergents, iodinated SEPHADEX® (See U.S. application Ser. Nos. 08/667,448 and 08/813,337), and gamma-irradiation of final container, all of which are useful viral reduction tools.

We have also achieved extremely promising results with pathogen inactivating compositions (See U.S. application Ser. No. 09/159,460 filed Sep. 24, 1998). PICs are produced by an aqueous extraction of a pathogen inactivating agent from iodinated ion exchange matrices, such as iodinated DEAE-SEPHADEX® (see U.S. application Ser. Nos. 08/667,448 and 08/813,337). Using PIC, we have achieved viral reduction of >4.0 $\log_{10}$ of porcine parvovirus (PPV) while maintaining 95% of the API Elastase Inhibitor activity.

G. Formulation and Finishing Options

The API intermediate is diafiltered into 0.020M sodium phosphate, 0.1M NaCl, pH 6.8–7.0 for freezing at −80° C. The formulation will depend on the viral inactivation step(s) selected and the intended mode of administration. For instance, as introduced in Table 1, depending on the disease being treated, API may be administered intravenously, as an aerosol, or as a topical treatment. Accordingly, the API may be stored as a lyophilized powder, a liquid or a suspension.

H. Evaluation of protein quantity and activity

Assays for determining the quantity and activity of API in a sample are known in the art and may be employed herein for evaluating the efficiency of the method. For instance, an immunoassay involving a monoclonal antibody specific for API for measuring or detecting API in biological fluids is disclosed in U.S. Pat. No. 5,114,863, hereby incorporated by reference.

Evaluation may also be performed by measuring inhibitory activity against the protease elastase as described in U.S. Pat. No. 4,697,003, also incorporated by reference. API activity is estimated by its elastase inhibitory capacity using a chromogenic substrate for elastase. Hydrolysis of N-succinyl-L-alanyl-L-alanyl-L-alanyl-p-nitroanilide (SA3pNA) by elastase causes an increase in absorption at 405 nm. This increase is continuously monitored, usually at 37° C. Comparisons of the linear changes of absorbance with time in the presence and absence of sample (API) are made. The amount of inhibitor is then calculated based on the known molecular weights of elastase and PI, on the known 1:1 stoichiometry, and on the known amount of elastase used. API may also be estimated by its trypsin inhibitory capacity in a similar manner.

Quantity of protein may also be determined by SDS PAGE, followed by any appropriate staining procedure, i.e., silver stain, or by Western analysis using a monoclonal antibody. SDS PAGE plus staining may also be used to assess purity of the sample and detect the presence of contaminating proteins.

I. Potential Variables

The following variations in column conditions have been evaluated and are acceptable for practicing the disclosed method. Process parameters for different anion exchange resins are given in Table 4, and process parameters for different cation exchange resins are given in Table 5. Conditions, i.e., pH and buffer type may be varied depending on the purity and yield desired. It is also conceivable that other similar columns may be optimized for use in the disclosed method. Accordingly, the following is not meant to be an exhaustive list.

TABLE 4

Process Parameters Evaluated for Various Anion Exchange Resins

| Anion Exchange Resins | Equilibration Buffer | Wash Buffer | Elution Buffer |
|---|---|---|---|
| DEAE SEPHAROSE ® FAST FLOW | 15–20 mM Na phosphate, pH 5.8–6.4 | 15–20 mM Na phosphate, pH 5.8–6.4 | 15–20 mM Na citrate pH 6.0–8.0 |
| DEAE SEPHAROSE ® CL-6B | 15–20 mM Na phosphate, pH 5.8–6.4 | 15–20 mM Na phosphate, pH 5.8–6.4 | 15–20 mM Na citrate pH 6.0–8.0 |
| Q SEPHAROSE ® FAST FLOW | 15–25 mM Na phosphate, pH 5.9–6.2 | 15–25 mM Na phosphate, pH 5.9–6.2 | 20–25 mM Na citrate pH 6.0–8.0 |

(Linear velocities: 20–60 cm/hour; minimal residence time of load in column of 6 minutes.)

TABLE 5

Process Parameters Evaluated for Various Cation Exchange Resins

| Cation Exchange Resins | pH of load+ | Conductivity & Column Equilibration ($m\Omega^{-1}$) | Equilibration Buffer Composition ($m\Omega^{-1}$ + pH) |
|---|---|---|---|
| CM SEPHAROSE ® FAST FLOW | 5.3–5.45 | 1.35–1.45 | 3–5 mM Na citrate, pH 5.3–5.45 |
| CM SEPHAROSE ® CL-6B | 5.2–5.35 | 0.9–1.30 | 3–5 mM Na citrate, pH 5.2–5.35 |
| SP SEPHAROSE ® FAST FLOW | 5.17–5.2 | 0.9–1.80 | 3–10 mM Na citrate, pH 5.2–5.35 |
| FRACTOGEL EMD $SO_3^-$-650 (m) | 5.3 | 1.33 | 3–5 mM Na citrate, pH 5.2–5.35 |
| WHATMAN-CELLULOSE ® | 5.2–5.36 | 1.1–1.53 | 4 mM Na citrate |

+Load: adjusted effluent of anion exchange column

EXAMPLE 1

Table 6 shows the quantities of API recovered at various stages of the method, as evaluated by activity and antigen assay. Starting material was 1.5 kg of Cohn Fraction IV-1 paste.

TABLE 6

API Recoveries of Pilot Lot 1.
Evaluation by Antigen and Activity.
(Processing of 1.5 kg Cohn IV-1)

| Description | Volume (L) | Total API-Array + (mg) | Step Yields (%) | Total API-Activity + + (mg) | Active API + + + (%) | cA280 × $1000^{-3}$ | Active API + + + (%) | Spec. Activity (mg active API/cA280) |
|---|---|---|---|---|---|---|---|---|
| Cohn IV-1 Susp.- DSSF Load (filtered) | 21.2 | 26,500 | 100 | 18,804 | 100 | 266.7 | 71 | 0.07 |
| DSFF Fall-through | 20.6 | 3,893 | 14.5 | 1,666 | 8.8 | 131.84 | 43 | |
| Wash | 18.4 | 677 | 2.6 | 379 | 2 | 13.08 | 56 | |
| Effluent Pool | 5.5 | 18,181 | 68.6 | 19,398 | 100 | 74.49 | 100 | 0.27 |
| CMS Load + + + + | 2.56 | 8,781 | 100 | 9,768 | 100 | 35.74 | | |
| CMS Fall-through pH adjusted | 9.3 | 6,612 | 75.3 | 6,670 | 68.3 | 5.78 | | |
| API Intermediate Concentrate | 0.664 | 5,717 | 65.1 | 6,662 | 68.2 | 4.01 | 100 | 1.66 |

+ Antigen (Nephelometry)
+ + Porcine Elaste Inhibitory

Column Volumes 2. L DSFF
2.0 L CMS

TABLE 6-continued

API Recoveries of Pilot Lot 1.
Evaluation by Antigen and Activity.
(Processing of 1.5 kg Cohn IV-1)

| Description | Volume (L) | Total API-Array + (mg) | Step Yields (%) | Total API-Activity + + (mg) | Active API + + + (%) | cA280 × $1000^{-3}$ | Active API + + + (%) | Spec. Activity (mg active API/cA280) |
|---|---|---|---|---|---|---|---|---|

Assay
+ + + Active API/API Antigen
+ + + + Approx. half of DSFF effluent pool before adjustment of pH and conductivity

EXAMPLE 2

Table 7 shows the quantities of API recovered at various stages in a second trial of the method, as evaluated by activity and antigen assay. Starting material for this example was 2.7 kg of Cohn Fraction IV-1 paste.

For this trial, LRA pre-treatment was employed to reduce the quantity of lipoprotein in the Cohn IV-1 suspension. As can be seen by comparing the results presented in Examples 1 and 2, LRA affects only column sizes, but not overall yields and purity of the final product.

and antigen assay. Starting material for this example was 3.2 kg of Cohn Fraction IV-1 paste. For this trial, LRA pre-treatment was also employed to reduce the quantity of lipoprotein in the Cohn IV-1 suspension.

Following CMS, the pH was adjusted to 6.6, and one part of the sample was immediately diafiltered, concentrated and lyophilized. The second part was nanofiltered and treated with Pathogen Inactivating Composition, then diafiltered, concentrated and lyophilized. The purity and activity of both lyophilized products was the same and >95%.

TABLE 7

API Recoveries of Pilot Lot 2.
Evaluation by Antigen and Activity.
(Processing of 2.7 kg Cohn IV-1 -LRA treated)

| Description | Volume (L) | Total API-Array + (mg) | Step Yields (%) | Total API-Activity + + (mg) | Active API + + + (%) | cA280 × $1000^{-3}$ | Active API + + + (%) | Spec. Activity (mg active API/cA280) |
|---|---|---|---|---|---|---|---|---|
| Cohn IV-1 Susp.- LRA treated DSFF Load | 46.7 | 49,502 | 100 | 25,260 | 100 | 427.3 | 51 | 0.059 |
| DSFF Fall-through | 46.5 | 12,276 | 24.8 | 0 | 0 | 218.08 | 0 | |
| Wash | 22.9 | 534 | 1.1 | 440 | 1.7 | 10.39 | 82 | |
| Effluent Pool | 5.5 | 21,285 | 42.9 | 20,050 | 79 | 82.94 | 94.2 | 0.024 |
| CMS Load + + + + | 2.5 | 9,675 | 100 | 9,120 | 100 | 37.7 | | |
| CMS Fall-through pH adjusted | 7.7 | ND | | | | | | |
| API Intermediate Concentrate | 0.73 | 7,446 | 77 | 9,125 | 100 | 4.9 | 100 | 1.86 |
| + Antigen (Nephelometry) | | | | Column Volumes | 2.0 L DSFF | | | |
| + + Porcine Elaste Inhibitory Assay | | | | | 2.0 L CMS | | | |

+ + + Active API/API Antigen
+ + + + Approx. half of DSFF effluent pool before adjustment of pH and conductivity

EXAMPLE 3

Table 8 shows the quantities of API recovered at various stages in a third trial of the method, as evaluated by activity Absorbance at A280 nm was monitored throughout the purification process, and the specific activity was calculated for the API after various steps.

TABLE 8

API Recoveries of Pilot Lot 3.
Evaluation by Antigen and Activity.
(Processing of 3.2 kg Cohn IV-1 -LRA treated)

| Description | Volume (L) | Total API-Array + (mg) | Step Yields (%) | Total API-Activity + + (mg) | Active API + + + (%) | cA280 × $1000^{-3}$ | Active API + + + (%) | Spec. Activity (mg active API/cA280) |
|---|---|---|---|---|---|---|---|---|
| Cohn IV-1 Susp.- LRA treated DSFF Load | 47.75 | 56,110 | 100 | 23,970 | 100 | 333.25 | 43 | 0.072 |
| DSFF Fall-through | 47.6 | 11,420 | 20.4 | 1,140 | 4.7 | 111.1 | 9.9 | |
| Wash | 65.2 | 2,050 | 3.6 | 1,240 | 5.17 | 33.51 | 60.5 | |
| Effluent Pool | 5 | 27,200 | 48.4 | 26,300 | 100 | 64.77 | 96.7 | 0.41 |
| CMS Load + + + + | 2.5 | 13,600 | 100 | 13,150 | 100 | | | |

TABLE 8-continued

API Recoveries of Pilot Lot 3.
Evaluation by Antigen and Activity.
(Processing of 3.2 kg Cohn IV-1 -LRA treated)

| API Intermediate Concentrate | 0.8 | 10,440 | 77 | 11,960 | 91 | 6.5 | 100 | 1.84 |
|---|---|---|---|---|---|---|---|---|
| Lyophilized Concentrates: | | API (mg/ml) | | API (mg/ml) | | cA280 | % Active | Spec. Activity |
| Lyophilized | | 12,650 | | 12,590 | | 6.12 | 100 | 2.05 |
| Lyophilized-nanofiltered/virally inactivated | | 4,490 | | 4,570 | | 2.2 | 100 | 2.07 |
| + Antigen (Nephelometry) | | | | Column Volumes: | 2.3 L DSFF | | | |
| + + Porcine Elaste Inhibitory Assay | | | | | 2.0 L CMS | | | |

+ + + Active API/API Antigen
+ + + Approx. half of DSFF effluent pool before adjustment of pH and conductivity So that the optimal purity of active API could be evaluated following each of the column steps, only half of the API eluted from the DSFF column for each of the trials was loaded onto the CM SEPHAROSE® column. As can be seen in Table 9, the recovery of API after the DSFF column step is normally between 96–100%. Most notably for the second and third trials, the fall-through following CMS column purification and a half column volume of post-wash contained >90% of the total load of active API.

TABLE 9

Process Recoveries and Specific Activities of API Lots

| Pilot | Amount of Cohn IV-1 (kg) | LRA | Step Yields+ DSFF | CMS | Overall Yield (%) | Spec Act.++ (mg/ c280 nm) |
|---|---|---|---|---|---|---|
| 1 | 1.5 | no | 100 | 68 | 68 | 1.66 |
| 2 | 2.7 | yes | 79 | 100 | 79 | 1.86 |
| 3 | 3.2 | yes | 100 | 91 | 91 | 1.95 |

+As determined by Porcine Elastase Inhibitory Assay
++Specific gravity of API was defined as mg of active API divided by Absorbance at 280–320 nm.

Examples 1–3 present trial runs of the method of the invention on a relatively small scale. The process may easily be scaled up for production of commercial quantities, using the following table as a guideline. To produce highly purified API from Cohn fraction IV-1, a DSFF resin of 0.85–1.0 L and a CM-SEPHAROSE ® resin of 1.7–2.0 L is recommended per kg of paste following LRA treatment at 4% (w/v). The yields of the large scale column process are >75% (usually between 80–90%) and fully active API is also provided. If LRA is omitted, the column sizes must be nearly doubled to achieve the same results.

TABLE 10

Summary of Process Volumes at Various Paste Weights with List of Column Sizes

| Process Volumes | Weight of Cohn IV-1 | | | | |
|---|---|---|---|---|---|
| | 5 kg | 10 kg | 20 kg | 40 kg | 70 kg |
| Cohn Susp. Dissol. Vol (L) | 75 | 150 | 300 | 600 | 1050 |
| Amount LRA* | 3.0 | 6.0 | 12.0 | 24.0 | 42.0 |
| DSFF Col Vol¹ (L) | 4.5 | 9.0 | 18.0 | 36 | 56–70 |

TABLE 10-continued

Summary of Process Volumes at Various Paste Weights with List of Column Sizes

| Process Volumes | Weight of Cohn IV-1 | | | | |
|---|---|---|---|---|---|
| | 5 kg | 10 kg | 20 kg | 40 kg | 70 kg |
| DSFF Effluent Vol (L) | 12.5 | 25 | 50 | 100 | 140–210 |
| CM-SEPHAROSE ® Col Vol² (L) | 9.0 | 18 | 36 | 72 | 126 |
| CMS - FT pool (L) | 45 | 90 | 180 | 360 | 630 |
| API final bulk @ 10 mg/ml | 4–5 L | 8–10 L | 16–20 L | 35–40 L | 55–70 L |
| Column Sizes | | | | | |
| DSFF | | | | | |
| Col. Diam. (cm)³ | 18 | 25 | | 45 | 63 |
| Col. Hgt. (cm) | 18 | 18 | | 11 | 20 |
| Velocity (cm/H) | 60 | 80 | | 60 | 60 |
| Load Time (H) | 4.9 | 3.8 | | 6.3 | 5.6 |
| DSFF | | | | | |
| Col. Diam. (cm)³ | 18 | 45 | 45 | 45 | 63 |
| Col. Hgt. (cm) | 18 | 5.6 | 11 | 23 | 20 |
| Velocity (cm/H) | 80 | 40 | 60 | 80 | 80 |
| Load Time (H) | 3.8 | 2.4 | 3.2 | 4.7 | 4.4 |
| CMS | | | | | |
| Col. Diam. (cm)⁴ | 25 | 45 | 45 | 45 | |
| Col. Hgt. (cm) | 18 | 5.6 | 23 | (46) | |
| Velocity (cm/H) | 40 | 20 | 40 | | |
| Load Time (H) | 2.3 | 2.8 | 2.8 | | |
| CMS | | | | | |
| Col. Diam. (cm)⁴ | 18 | 45 | | 63 | 63 |
| Col. Hgt. (cm) | 36 | 5.6 | | 23 | 23 |
| Velocity (cm/H) | 60 | 30 | | 40 | 60 |
| Load Time (H) | 2.9 | 1.9 | | 2.9 | 3.4 |

¹Ranges of DEAE-SEPHAROSE ®, Fast Flow (DSFF): 0.8–1.0 per kg of input paste
²Ranges of CM-SEPHAROSE ®, Fast Flow (CMS): 1.6–1.9 per kg of input paste
³DSFF residence time > 8 minutes
⁴CMS residence time > 15 minutes
*One kg of LRA produces 5 kg of precipitate, which is collected by filter-press with appropriately sized frames.

The method of the present invention enables separation of active API from inactive API. It has been surprisingly found that this separation occurs in a single ion exchange chromatography step. To more clearly demonstrate this result, the percent of active API before and after DEAE chromatography for each of the trial runs is presented in Table 11.

TABLE 11

DEAE-SEPHAROSE ® Separates Active API from
Inactive API (Distribution of API by Antigen and
Activity)

| DEAE chromatography run | API - Antigen[+] (g) | API - Activity[++] (g) | % active API before & after DEAE chroma. |
|---|---|---|---|
| Pilot 1 | | | |
| Load | 26.9 | 18.8 | 71 |
| Elution | 18.1 | 18.6 | 100 |
| Pilot 2 | | | |
| Load | 49 | 25 | 51 |
| Elution | 21 | 20 | 94 |
| Pilot 3 | | | |
| Load | 56 | 24 | 43 |
| Elution | 21 | 26 | 97 |

[+]Array
[++]Porcine Elastase Inhibitor Assay

As can be seen by the above results, the method of the present invention results in API recovery of >70% from Cohn Fraction IV-1, with 100% activity. Thus, the method selectively purifies active API. The process may be easily scaled up for processing of a manufacturing lot of at least 70 kg with virtually no loss in processing time (i.e., 20–22 hrs for a 70 kg lot). Moreover, the process is applicable with minor changes (reduction in resin volumes) to other Cohn fraction sources of similar composition.

The present invention further provides API formulations substantially free of other human proteins, and wherein the protein content is at least about 90% active API. Heretofore, similar formulations suffered from the inability to separate active from inactive API and/or the inability to purify and isolate API (whether active or inactive) from other proteins in the starting material (e.g., the proteins of Cohn Fraction IV-1 described above). Now it is possible to create formulations of API of greater than 90% pure API, and of that API as much as 100% is active API.

The present invention further affords pharmaceutical formulations comprising therapeutically effective amounts of active API of at least about 90% purity in combination with pharmaceutically acceptable excipients and/or adjuvants. Pharmaceutically acceptable excipients include solvents, carriers, buffers, preservatives, and other pharmacologically inert materials contributing to the stability of the formulation.

What is claimed is:

1. A method for purifying alpha-1 proteinase inhibitor comprising:
   (i) suspending an unpurified mixture of proteins containing API in non-citrate based buffer;
   (ii) removing lipoproteins from said protein suspension with lipid removal agent;
   (iii) contacting the resulting protein suspension with an anion exchange resin and washing said resin with a non-citrate based buffer;
   (iv) eluting an active API-containing fraction from said anion exchange resin with a citrate based buffer;
   (v) contacting the API-containing fraction of step (iv) with a cation exchange resin in the presence of a citrate based buffer; and
   (vi) collecting purified, active API in the effluent of step (v).

2. The method of claim 1, wherein said protein suspension is adjusted to a pH of between about 5 and about 7 before being loaded onto the anion exchange resin.

3. The method of claim 1, wherein said unpurified mixture of proteins is selected from the group consisting of: a Cohn Fraction, a combination of Cohn Fractions, human blood plasma, fractions of human blood plasma, and milk.

4. The method of claim 1, wherein said unpurified mixture of proteins is Cohn Fraction IV-1 paste.

5. The method of claim 1, wherein said anion exchange resin is a DEAE-derivatized agarose resin.

6. The method of claim 1, wherein said cation exchange resin is a carboxymethyl-derivatized agarose resin.

7. A pharmaceutical formulation comprising a therapeutically effective amount of API in combination with pharmaceutically acceptable excipients, wherein said API is at least about 95% active API and wherein said pharmaceutical formulation is produced by the method of claim 1.

8. A formulation comprising API wherein at least about 90% of all API in said formulation is active API, and wherein said formulation is produced by the method of claim 1.

9. The method of claim 1, wherein said non-citrate based buffer is sodium phosphate buffer.

10. The method of claim 9, wherein said sodium phosphate buffer is at a pH of between about 6 and about 9.

11. The method of claim 1, wherein said citrate based buffer is sodium citrate.

12. The method of claim 11, wherein said sodium citrate is at a pH of between about 5.5 and about 8.5 for the elution of active API.

13. The method of claim 1, wherein said API-containing fraction from said anion exchange resin is adjusted to a pH of less than 5.6 and to a conductivity of less than 1.7 mmho before being contacted with the cation exchange resin.

14. The method of claim 13, wherein said pH is between about 5 and about 5.5, and said conductivity is between about 0.9 and about 1.6 mmho.

15. The method of claim 1, wherein the purified, active API is further subjected to viral reduction.

16. The method of claim 15, wherein said viral reduction is accomplished by nanofiltration.

17. The method of claim 15, wherein said viral reduction is accomplished by treatment with an iodinated ion exchange matrix material.

18. The method of claim 15, wherein said viral reduction is accomplished by contacting said purified, active API with a pathogen inactivating composition.

19. The method of claim 15, wherein said viral reduction is accomplished by combining any or all of nanofiltration, treatment with an iodinated ion exchange matrix material, and contact with a pathogen inactivating composition.

20. A method for separating active from inactive API to produce API fractions of at least about 90% active API, said method comprising:
   (i) suspending an unpurified mixture of proteins containing both active and inactive API in a phosphate buffer;
   (ii) removing lipoproteins from said protein suspension with lipid removal agent;
   (iii) loading the resulting protein suspension on an anion exchange resin, and washing said resin with a phosphate based buffer; and
   (iv) eluting and collecting API from said resin with a citrate based buffer.

21. The method of claim 20, wherein said citrate buffer is first adjusted to a pH of about 6.0.

22. The method of claim 20, wherein said anion exchange resin is an agarose based resin derivatized with either a tertiary or quaternary amine functional group.

23. The method of claim 20, wherein said anion exchange resin is a DEAE-derivatized resin, and wherein said resin is formed from a matrix selected from the group consisting of agarose, cellulose, and acrylamide.

24. The method of claim 20, wherein said unpurified mixture of proteins is Cohn Fraction IV-1 paste.

25. The method of claim 20, wherein said phosphate buffer suspension of step (i) is adjusted to a pH of about 5.8 to about 6.4 prior to loading said suspension on said anion exchange resin.

26. The method of claim 25, wherein said phosphate buffer is sodium phosphate.

27. The method of claim 26, wherein said sodium phosphate buffer is first adjusted to a pH of about 6.0 prior to loading said suspension on said anion exchange resin.

28. A method for purifying API comprising:
 (i) suspending an unpurified mixture of proteins containing API in a phosphate buffer;
 (ii) removing lipoproteins from said protein suspension with lipid removal agent;
 (iii) contacting the resulting protein suspension with an anion exchange resin and washing said resin with a phosphate buffer;
 (iv) eluting an active API-containing fraction from said anion exchange resin with a citrate buffer;
 (v) adjusting the citrate buffer of the API-containing fraction to a pH of about 5.0 to about 5.5 and a conductivity of about 0.9 to about 1.6 mmho;
 (vi) contacting the pH- and conductivity-adjusted API-containing fraction of step (v) with a cation exchange resin; and
 (vii) collecting purified, active API in a citrate buffer wash of the cation exchange resin of step (vi).

29. A method for purifying API comprising
 (i) creating a suspension of Cohn Fraction IV-1 paste in sodium phosphate buffer;
 (ii) treating the suspension with lipid removal agent and clarifying the suspension;
 (iii) loading the clarified suspension of step (ii) on a DEAE-derivatized, agarose based anion exchange resin and washing said resin with a sodium phosphate buffer;
 (iv) eluting an active API-rich fraction from said loaded anion exchange resin with a sodium citrate buffer;
 (v) adjusting the active API-rich sodium citrate eluate of step (iv) to a pH of between about 5.0 to about 5.5 and a conductivity of between about 1.3 to about 1.45 mmho;
 (vi) contacting the pH- and conductivity-adjusted API-rich eluate of step (v) with a carboxymethyl agarose cation exchange resin; and
 (vii) collecting purified, active API in the effluent of step (vi).

30. The method of claim 29, wherein said phosphate buffer mixture of step (i) is adjusted to a pH of about 6.0 before treatment with lipid removal agent and before contact with said anion exchange resin.

31. The method of claim 29, wherein said sodium citrate buffer of step (iv) is adjusted to a pH of about 6.0.

32. The method of claim 29, wherein the API of the fraction of step (iv) is at least about 90% active API.

33. The method of claim 29, wherein the API of the fraction of step (vi) is at least about 95% active API.

* * * * *